United States Patent [19]

Ueda et al.

[11] Patent Number: 4,562,190
[45] Date of Patent: Dec. 31, 1985

[54] BENZOTHIAZOLONE DERIVATIVES, PROCESSES FOR PREPARATION THEREOF AND PHARMACEUTICAL COMPOSITIONS COMPRISING THE SAME

[75] Inventors: Ikuo Ueda, Uenohigashi; Kiyoshi Taniguchi, Osaka; Yousuke Katsura, Uenonishi, all of Japan

[73] Assignee: Fujisawa Pharmaceutical Co., Ltd., Osaka, Japan

[21] Appl. No.: 627,612

[22] Filed: Jul. 3, 1984

[30] Foreign Application Priority Data

Jul. 25, 1983 [GB] United Kingdom ................ 8320005

[51] Int. Cl.⁴ ................ C07D 417/02; C07D 417/06; C07D 417/10; C07D 417/14
[52] U.S. Cl. .................................... 514/254; 544/238; 544/369; 548/170; 548/171; 546/209; 260/239 A; 260/239 B; 260/239 BC
[58] Field of Search ................ 544/238, 369; 548/171, 548/170; 424/250, 270; 514/254; 546/209; 260/239 A, 239 B, 239 BC

[56] References Cited

U.S. PATENT DOCUMENTS

| | | | |
|---|---|---|---|
| 3,839,349 | 10/1974 | Wagner et al. | 424/270 |
| 4,258,185 | 3/1981 | Nakao et al. | 544/238 |
| 4,361,563 | 11/1982 | Austel | 544/238 |
| 4,370,340 | 1/1983 | Ueda et al. | 548/170 |

FOREIGN PATENT DOCUMENTS

| | | | |
|---|---|---|---|
| 71102 | 2/1983 | European Pat. Off. | |
| 54-16485 | 2/1979 | Japan | 544/238 |
| 59-53479 | 3/1984 | Japan | 544/238 |

Primary Examiner—Veronica P. Hoke
Attorney, Agent, or Firm—Oblon, Fisher, Spivak, McClelland & Maier

[57] ABSTRACT

A compound of the formula:

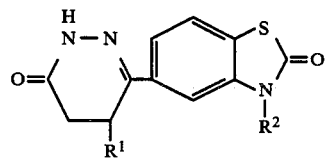

wherein
$R^1$ is lower alkyl, and
$R^2$ is hydrogen lower alkyl, carboxy(lower)alkyl, lower alkoxy(lower)alkyl, aliphatic acyl (lower)alkyl, aromatic acyl(lower)alkyl or heterocyclic acyl(lower)alkyl, and pharmaceutically acceptable salts thereof are useful for treatment of hypertension, heart disease and thrombosis.

8 Claims, No Drawings

BENZOTHIAZOLONE DERIVATIVES, PROCESSES FOR PREPARATION THEREOF AND PHARMACEUTICAL COMPOSITIONS COMPRISING THE SAME

The present invention relates to novel benzothiazolone derivatives and pharmaceutically acceptable salt thereof. More particularly, it relates to novel benzothiazolone derivatives and pharmaceutically acceptable salts thereof which have antihypertensive activity, cardiotonic activity and inhibitory activity on platelet aggregation, to processes for preparation thereof, to pharmaceutical composition comprising the same, and to a method of using the same therapeutically in the treatment of hypertension, heart disease and thrombosis in human being and animals.

Accordingly, one object of this invention is to provide novel benzothiazolone derivatives and pharmaceutically acceptable salts thereof, which are useful as an antihypertensive agent, cardiotonic and antithrombotic agent.

Another object of this invention is to provide processes for preparation of said benzothiazolone derivatives and pharmaceutically acceptable salts thereof.

A further object of this invention is to provide pharmaceutical composition comprising, as an active ingredient, said benzothiazolone derivative or its pharmaceutically acceptable salt.

Still further object of this invention is to provide a method of using said benzothiazolone derivative or its pharmaceutically acceptable salt in the treatment of hypertension, heart disease and thrombosis in human being and animals.

The object compounds of the present invention can be represented by the following formula (I).

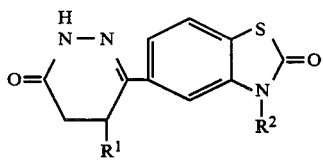

(I)

wherein
$R^1$ is lower alkyl; and
$R^2$ is hydrogen or lower alkyl which may have suitable substituent(s).

According to the present invention, the new benzothiazolone derivatives (I) can be prepared by various processes which are illustrated in the following schemes.

Process 1

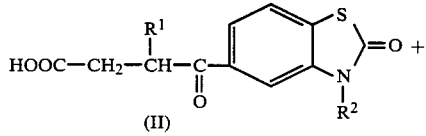

(II)
or its reactive derivative
at the carboxy group
or a salt thereof

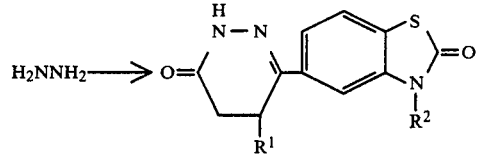

(III)            (I)
or its hydrate      or a salt thereof
or a salt thereof

Process 2

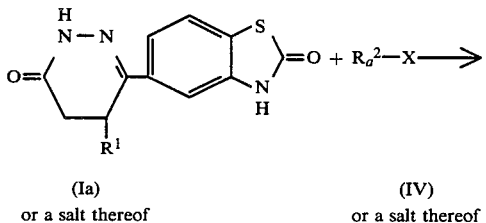

(Ia)            (IV)
or a salt thereof    or a salt thereof

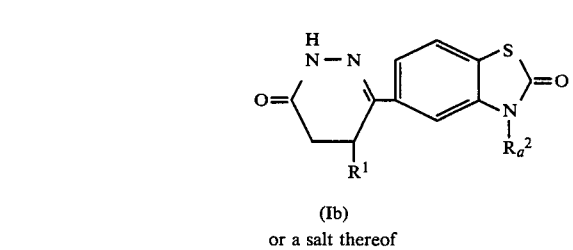

(Ib)
or a salt thereof

Process 3

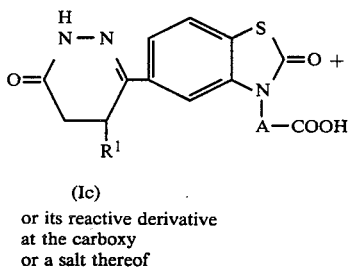

(Ic)
or its reactive derivative
at the carboxy
or a salt thereof

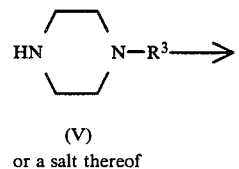

(V)
or a salt thereof

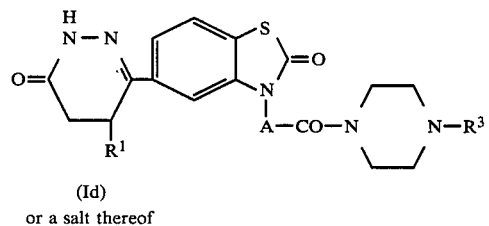

(Id)
or a salt thereof wherein
$R^1$ and $R^2$ are each as defined above,
$R_a^2$ is lower alkyl which may have suitable substituent(s), X is an acid residue,
A is lower alkylene, and
$R^3$ is lower alkyl which may be substituted with suitable substituent(s).

The starting compound (II) is novel and can be prepared by the following Processes.

Process A

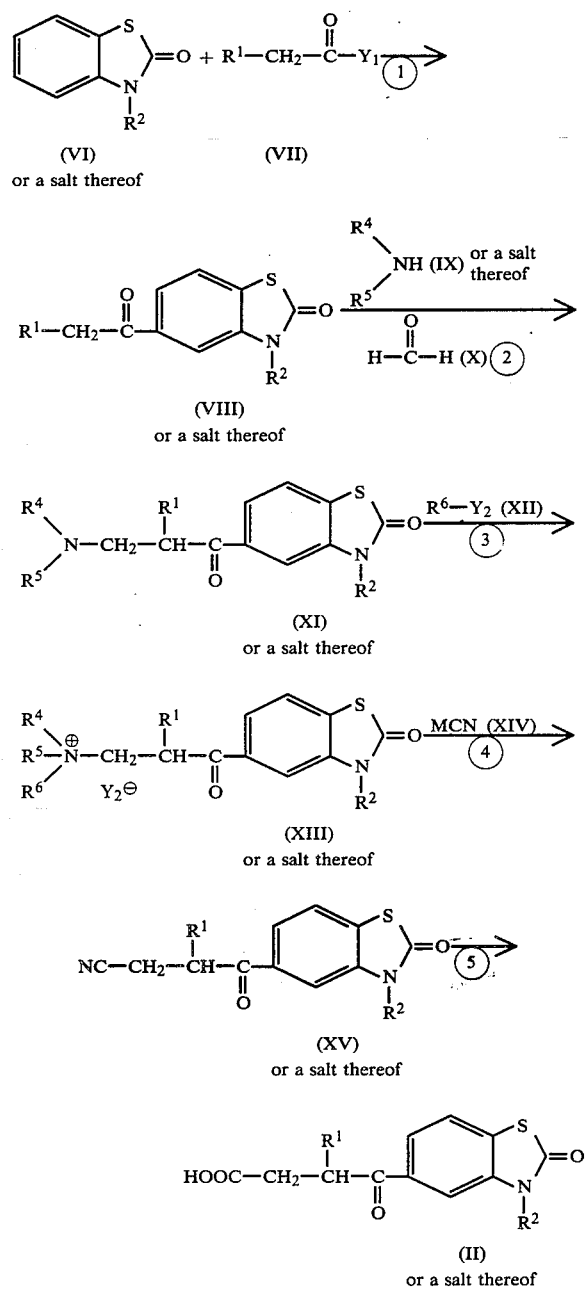

wherein
$R^1$ and $R^2$ are each as defined above,
$Y_1$ is halogen,
$R^4$ is lower alkyl,
$R^5$ is lower alkyl,
$R^6$ is lower alkyl,
$Y_2$ is halogen, and M is an alkali metal.

Suitable pharmaceutically acceptable salts of the object compounds (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "lower alkyl" and "lower alkyl moiety" in the terms "lower alkyl which may have suitable substituent(s)" and "lower alkyl which may be substituted with suitable substituent(s)" may include methyl, ethyl, propyl, isopropyl, butyl, t-butyl, pentyl, hexyl and the like, preferably one having 1 to 4 carbon atom(s).

Suitable "substituent" in the term "lower alkyl which may have suitable substituent(s)" may include carboxy, lower alkoxy (e.g., methoxy, ehtoxy, propoxy, isopropoxy, butoxy, t-butoxy, pentyloxy, hexyloxy, etc.), acyl as mentioned below, and the like.

Suitable "acyl" may include aliphatic acyl group, acyl group containing an aromatic ring or a heterocyclic ring, which is referred to as aromatic acyl or heterocyclic acyl, and the like.

Suitable example of said acyl may be illustrated as follows:-

Aliphatic acyl such as lower alkoxycarbonyl (e.g., methoxycarbonyl, ethoxycarbonyl, propoxycarbonyl, butoxycarbonyl, t-butoxycarbonyl, pentyloxycarbonyl, hexyloxycarbonyl, etc.), or the like;

Heterocyclic acyl such as heterocycliccarbonyl (e.g., piperazinylcarbonyl, etc.), or the like.

Suitable heterocyclic moiety in the term "heterocycliccarbonyl" may include saturated 3 to 8-membered (more preferably 5 or 6-membered) heteromonocyclic group containing 1 to 4 nitrogen atom(s), for example, pyrrolidinyl, imidazolidinyl, piperidino, piperazinyl, etc.; and the like.

The acyl moiety as stated above may have suitable substituent(s) such as lower alkyl (e.g., methyl, ethyl, propyl, isopropyl, butyl, t-butyl, pentyl, hexyl, etc.), hydroxy(lower)alkyl (e.g., hydroxymethyl, 1(or 2)-hydroxyethyl, 1(or 2 or 3)-hydroxypropyl, 1(or 2 or 3 or 4)-hydroxybutyl, 1(or 2 or 3 or 4 or 5)-hydroxypentyl, 1(or 2 or 3 or 4 or 5 or 6)-hydroxyhexyl, etc.) or the like.

Suitable "acid residue" may include halogen (e.g., chlorine, bromine, fluorine or iodine), arenesulfonyloxy (e.g., tosyloxy) and the like.

Suitable "lower alkylene" may include methylene, ethylene, trimethylene, tetramethylene, pentamethylene, hexamethylene and the like, preferably one having 1 to 4 carbon atom(s).

Suitable "substituent" in the term "lower alkyl which may be substituted with suitable substituent(s)" may include hydroxy and the like.

Suitable "halogen" may include chlorine, bromine, fluorine and iodine.

Suitable "alkali metal" may include sodium, potassium and the like.

Preferred embodiments of the object compound (I) are as follows. Preferred embodiment of $R^1$ is lower alkyl; $R^2$ is hydrogen, lower alkyl, lower alkoxy(lower-)alkyl, lower alkoxycarbonyl(lower)alkyl or hydroxy(lower)alkylpiperazinylcarbonyl(lower)alkyl.

The processes for preparing the object compound of the present invention are explained in detail in the following.

Process 1

The compound (I) or a salt thereof can be prepared by reacting the compound (II) or its reactive derivative at the carboxy group or a salt thereof with the compound (III) or its hydrate or a salt thereof.

Suitable salt of the compound (III) may include an acid addition salt such as an organic acid salt (e.g. acetate, maleate, tartrate, methanesulfonate, benzenesulfonate, toluenesulfonate, etc.) or an inorganic acid salt (e.g. hydrochloride, hydrobromide, sulfate, phosphate, etc.), and the like.

Suitable salt of the compound (II) can be referred to the ones as exemplified for the compound (I).

Suitable reactive derivative at the carboxy group of the compound (II) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, ethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (II) to be used.

The reaction is usually carried out in the presence of a solvent such as alcohol (e.g., methanol, ethanol, etc.), acetone, dioxane, acetonitrile, chloroform, methylene chloride, ethylene chloride, tetrahydrofuran, ethyl acetate, N,N-dimethylformamide, or any other solvent which does not adversely influence the reaction.

The reaction temperature is not critical and the reaction is usually carried out under warming or heating.

Process 2

The compound (Ib) or a salt thereof can be prepared by reacting the compound (Ia) or a salt thereof with the compound (IV) or a salt thereof. Suitable salt of the compound (Ia) can be referred to the ones as exemplified for the compound (III). Suitable salts of the compounds (Ib) and (IV) can be referred to the ones as exemplified for the compound (I).

The present reaction is preferably carried out in the presence of a conventional base.

Suitable base includes, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g. sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as alkali metal acetate (e.g., sodium acetate, potassium acetate, etc.), alkali metal alkoxide (e.g., sodium methoxide, sodium ethoxide, sodium propoxide, etc.), trialkylamine (e.g., trimethylamine, triethylamine, etc.), or the like.

The reaction is usually carried out in a conventional solvent such as acetone, dioxane, acetonitrile, chloroform, methylene chloride, ethylene chloride, tetrahydrofuran, ethyl acetate, N,N-dimethylformamide, or any other solvent which does not adversely influence the reaction.

The reaction temperature is not critical and the reaction is usually carried out under cooling to warming.

Process 3

The compound (Id) or a salt thereof can be prepared by reacting the compound (Ic) or its reactive derivative at the carboxy group or a salt thereof with the compound (V) or a salt thereof. Suitable salts of the compound (Ic), (Id) and (V) can be referred to the ones as exemplified for the compound (I).

Suitable reactive derivative at the carboxy group of the compound (Ic) can be referred to the ones as exemplified for the compound (II). The reaction can be carried out in the absence or presence of a solvent such as acetone, dioxane, acetonitrile, chloroform, methylene chloride, ethylene chloride, tetrahydrofuran, ethyl acetate, N,N-dimethylformamide, or any other solvent which does not adversely influence the reaction. The reaction temperature is not critical and the reaction is usually carried out under warming or heating. The processes for preparing the starting compound (II) of the present invention are explained in the following.

Process A— ①

The compound (VIII) or a salt thereof can be prepared by reacting the compound (VI) or a salt thereof with the compound (VII).

The present reaction is preferably carried out in the presence of a catalyst such as aluminum halide (e.g., aluminum chloride) or the like.

The reaction is usually carried out in a conventional solvent such as carbon disulfide or any other solvent which does not adversely influence the reaction. The reaction temperature is not critical and the reaction is usually carried out under cooling to warming.

Process A— ②

The compound (XI) or a salt thereof can be prepared by reacting the compound (VIII) or a salt thereof with a mixture of the compound (IX) or a salt thereof and the compound (X).

The reaction is usually carried out in a conventional solvent such as acetic anhydride, alcohol (e.g., methanol, ethanol, etc.) or any other solvent which does not adversely influence the reaction.

The reaction temperature is not critical and the reaction is usually carried out under warming or heating.

Process A— ③

The object compound (XIII) or a salt thereof can be prepared by reacting the compound (XI) or a salt thereof with the compound (XII).

The reaction is usually carried out in a conventional solvent such as tetrahydrofuran or any other solvent which does not adversely influence the reaction.

The reaction temperature is not critical and the reaction is usually carried out under warming or heating.

Process A— ④

The compound (XV) or a salt thereof can be prepared by reacting the compound (XIII) or a salt thereof with the compound (XIV).

Suitable salts of the compounds (XIII) and (XV) can be referred to the ones as exemplified for the compound (I).

The reaction is usually carried out in a conventional solvent such as water acetone, dioxane, acetonitrile, chloroform, methylene chloride, ethylene chloride, tetrahydrofuran, ethyl acetate, N,N-dimethylformamide, or any other solvent which does not adversely influence the reaction.

The reaction temperature is not critical and the reaction is usually carried out at ambient temperature, under warming or under heating.

Process A— ⑤

The compound (II) or a salt thereof can be prepared by subjecting the compound (XV) or a salt thereof to hydrolysis.

Hydrolysis is preferably carried out in the presence of a base or an acid. Suitable base may include alkali metal hydroxide (e.g., sodium hydroxide, potassium hydroxide, etc.), alkali metal carbonate (e.g., sodium carbonate, potassium carbonate, etc.), alkali metal bicarbonate (e.g., sodium bicarbonate, potassium bicarbonate, etc.), alkaline earth metal hydroxide (e.g., calcium hydroxide, magnesium hydroxide, etc.), alkaline earth metal carbonate (e.g., calcium carbonate, magnesium carbonate, etc.) and the like.

Suitable acid may include an organic acid (e.g., formic acid, acetic acid, propionic acid, trifluoroacetic acid, etc.) and an inorganic acid (e.g., hydrochloric acid, hydrobromic acid, sulfuric acid, etc.).

The reaction is usually carried out in a solvent such as water, acetone, dioxane, chloroform, methylene chloride, ethylene chloride, tetrahydrofuran, N,N-dimethylformamide, or any other solvent which does not adversely influence the reaction.

A liquid base or acid can be also used as the solvent. The reaction temperature is not critical and the reaction is usually carried out under warming or under heating.

The following antihypertensive test data, cardiotonic test data and inhibitory activity test data on platelet aggregation show that the compound (I) of the present invention exhibit antihypertensive activity, cardiotonic activity and inhibitory activity on platelet aggregation, and are useful as an antihypertensive agent, cardiotonic and antithrombotic agent.

[1] Antihypertensive activity (A) Test Method

Five-week old male Wistar rats were uninephrectomized under anesthesia. Deoxycorticosterone acetate (DOCA) (30 mg/kg), suspended in peanut oil, was injected subcutaneously twice a week and 1% saline was substituted for the drinking water. Animals with mean blood pressure 150–200 mmHg were used for experiment between 5 and 7 weeks after surgery.

The test compound was administered orally. Blood pressure was measured at the femoral artery by means of a pressure transducer and recorded as electrically integrated values of mean arterial pressure.

(B) Test Compound

3-Methyl-5-(4-methyl-6-oxo-1,4,5,6-tetrahydro-3-pyridazinyl)benzothiazolone (test compound ① ).

(C) Test Results

Mean ratios of maximum decrease of blood pressure (mmHg) are shown in the following table.

| Test Compound | Dose (mg/kg) | Effect Max (%) |
|---|---|---|
| test compound ① | 1.0 | 63 |

[2] Cardiotonic activity (A) Test Method

Mongrel dogs of either sex were anesthetized with sodium pentobarbital, 35 mg/kg, i.p.. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure, from which dp/dt max was derived by analog computing. To measure the systemic blood pressure the left femoral artery was cannulated. The blood pressure pulses was used to trigger a heart rate meter. Another catheter was positioned in the vena cava through right femoral vein for injection of drug. Systemic blood pressure, left ventricular pressure, dp/dt max and heart rate were recorded simultaneously on a polygram (Nihonkohden, RJG-4008).

Test compound was dissolved in dimethyl sulfoxide (0.04 ml/kg) and injected into the femoral vein. The parameters after dosing were compared with those during the predosing period.

Test results were represented in terms of percentage of dp/dt max changes (dp/dt M.C.) and percentage of heart rate changes (H.R.C.) calculated by following formulae.

$$dp/dt\ M.C.\ (\%) = \left( \frac{dp/dt\ \text{max after dosing}}{dp/dt\ \text{max before dosing}} - 1 \right) \times 100$$

$$H.R.C.\ (\%) = \left(\frac{\text{heart rate after dosing}}{\text{heart rate before dosing}} - 1\right) \times 100$$

(B) Test Compound

3-Ethoxycarbonylmethyl-5-(4-methyl-6-oxo-1,4,5,6-tetrahydro-3-pyridazinyl)benzothiazolone (test compound ②).

(C) Test Results

| Test Compound | Dosage (mg/kg) | dp/dt M.C. (%) | H.R.C. (%) |
|---|---|---|---|
| test compound ② | 1 | 63 | 22 |

[3] Inhibitory activity on platelet aggregation (A) Test Method

Platelet rich plasma (PRP) which contains $6.5-7.5 \times 10^8$ platelet/ml was prepared from rabbit blood. To the 200 μl of PRP, 5 μl of calcium chloride (1mM) and 50 μl of pH 7.4 Tris-acetate solution (5 mM) containing 120mM NaCl and test compound was added successively, and then stirred for 2 min. at 37° C. To the solution 5 μl of adenosine diphosphate (ADP) (2.5 μM) or collagen (2.5 μg/ml) was added as an aggregation inducer. Aggregation was measured by using an aggregometer (NKK HEMA TRACER 1).

(B) Test Compound 5-(4-Methyl-6-oxo-1,4,5,6-tetrahydro-3-pyridazinyl)-benzothiazolone (test compound ③).

(C) Test Results

| Test Compound | ID$_{50}$ (Mol) ADP | ID$_{50}$ (Mol) Collagen |
|---|---|---|
| test compound ③ | $6.1 \times 10^{-8}$ | $3.5 \times 10^{-8}$ |

As being apparent from the above test results, the object compounds (I) of the present invention are useful as an antihypertensive agent, cardiotonic and antithrombotic agent.

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as capsule, tablet, dragee or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 0.01 mg/kg to 500 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

Propionyl chloride (113 ml) was added to a suspension of benzothiazolone (70 g) and aluminum chloride (246 g) in carbon disulfide (350 ml) at room temperature with stirring. The mixture was refluxed for 90 hours and cooled, and carbon disulfide was removed by decantation. The residue was poured into a mixture of cold water (3l) and methylene chloride (0.9 l).

The resulting precipitate was collected by filtration and chromatographed on silica gel by eluting with a mixture of chloroform and methanol (50:1) to give brown powder (28.5 g), which was recrystallized from tetrahydrofuran to give 5-propionylbenzothiazolone (21.5 g) as light red-violet crystals.

mp 210° to 212° C.

IR (Nujol): 3340, 3270, 1680, 1660 cm$^{-1}$

NMR (DMSO-d$_6$, δ): 1.10 (3H, t, J=7Hz), 3.00 (2H, q, J=7Hz), 7.18 (1H, d, J=8Hz), 7.88 (1H, dd, J=8Hz and 2Hz), 8.17 (1H, d, J=2Hz), 12.17 (1H, broad s)

Analysis Calcd. for C$_{10}$H$_9$NO$_2$S: C, 57.95; H, 4.38; N, 6.76. Found: C, 57.81; H, 4.41; N, 6.74.

Preparation 2

Acetic anhydride (70 ml) was added to a solution of dimethylamine hydrochloride (12.7 g) in 37% aqueous solution (10.5 ml) of formaldehyde at 80° C. To the solution was added 5-propionylbenzothiazolone (21.5 g) and the resultant mixture was stirred at the same temperature for 2 hours. After the solvent was evaporated in vacuo, the residue was treated with a mixture of saturated aqueous solution of sodium bicarbonate and ethyl acetate. Insoluble powder was collected by filtration to give 5-(3-dimethylamino-2-methylpropionyl)-benzothiazolone (12.5 g) as light red-violet powder.

mp 158° C. (dec.)

IR (Nujol): 1680, 1650 cm$^{-1}$

NMR (DMSO-d$_6$, δ): 1.09 (3H, d, J=7Hz), 2.02–2.87 (3H, m), 2.17 (6H, s), 3.52–4.10 (1H, m), 7.23 (1H, d, J=8Hz), 7.93 (1H, dd, J=8Hz and 2 Hz), 7.95 (1H, s), 8.23 (1H, d, J=2Hz)

Preparation 3

Methyl iodide (5.04 ml) was added to a solution of 5-(3-dimethylamino-2-methylpropionyl)benzothiazolone (18.0 g) in tetrahydrofuran (350 ml) and the mixture was heated at 70° C. for 1 hour. The resulting precipitate was collected by filtration and washed with tetrahydrofuran to give light red-violet powder (26.8 g), which was recrystallized from a mixture of methanol and water to give 5-[2-methyl-3-(trimethylammonio)-propionyl]benzothiazolone iodide as colorless needles.

mp 245° to 247° C.

IR (Nujol): 3060, 1690, 1670 cm$^{-1}$

NMR (DMSO-d$_6$, δ): 1.26 (3H, d, J=7Hz), 3.13 (9H, s), 3.43–4.22 (3H, m), 7.14 (1H, d, J=7Hz and 2Hz), 8.53 (1H, d, J=2Hz)

Analysis Calcd. for C$_{14}$H$_{19}$IN$_2$O$_2$S: C, 41.39; H, 4.71; N, 6.89. Found: C, 41.46; H, 4.50; N, 6.56.

Preparation 4

A solution of potassium cyanide (9.10 g) in water (28 ml) was added to a solution of 5-[2-methyl-3-(trimethylammonio)propionyl]benzothiazolone iodide (26.0 g) in water (400 ml). The mixture was refluxed for 1.5 hours, cooled and acidified with concentrated hydrochloric acid (12 ml). The resulting precipitate was collected and dissolved in ethyl acetate. The solution was washed with water, dried over magnesium sulfate and evaporated in vacuo to give light brown amorphous product (13.6 g). This (0.5 g) was purified by silica gel column chromatography and recrystallized from a mixture of ethyl acetate and n-hexane for analysis to give 5-(3-cyano-2-methylpropionyl)benzothiazolone (0.19 g) as slightly brown prisms.

mp 160° to 162° C.

IR (Nujol): 3250, 2250, 1670, 1650 cm$^{-1}$

NMR (DMSO-d$_6$, δ): 1.24 (3H, d, J=5Hz), 2.77 (2H, d, J=7Hz), 3.68–4.24 (1H, m), 7.23 (1H, d, J=9Hz), 7.96 (1H, dd, J=9Hz, and 2Hz), 8.29 (1H, d, J=2Hz), 12.00 (1H, broad s)

Preparation 5

A solution of 5-(3-cyano-2-methylpropionyl)benzothiazolone (13.0 g) is concentrated hydrochloric acid (65 ml) was refluxed for 1 hour with stirring. The mixture was basified with 20% aqueous solution of sodium hydroxide and washed with ethyl acetate. The aqueous layer was acidified with concentrated hydrochloric acid and the resulting precipitate was extracted with ethyl acetate. The extract was washed with water, dried over magnesium sulfate and evaporated in vacuo to give light brown product (12.9 g), which was recrystallized from a mixture of isopropyl alcohol and diisopropyl ether to give 5-(3-carboxy-2-methylpropionyl)benzothiazolone as colourless needles.

mp 166°πto 168° C.

IR (Nujol): 3325, 3090, 1690, 1670 cm$^{-1}$

NMR (DMSO-d$_6$, δ): 1.13 (3H, d, J=8Hz), 2.19–3.03 (1H, m), 3.60–4.10 (2H, m), 7.24 (1H, d, J=9Hz), 7.95 (1H, dd, J=9Hz and 2Hz), 8.27 (1H, d, J=2Hz), 12.17 (2H, broad s)

EXAMPLE 1

A solution of 5-(3-carboxy-2-methylpropionyl)benzothiazolone (11.8 g) and hydrazine hydrate (2.15 ml) in ethanol (120 ml) was refluxed for 1.5 hours with stirring. The resultant solid was collected by filtration and washed with ethanol to give pale yellow powder (7.10 g), which was recrystallized from methanol to afford 5-(4-methyl-6-oxo-1,4,5,6-tetrahydro-3-pyridazinyl)benzothiazolone as slightly yellow crystals.

mp 317° to 319° C.

IR (Nujol): 3175, 3070, 1725, 1685, 1650 cm$^{-1}$

NMR (DMSO-d$_6$, δ): 1.10 (3H, d, J=7Hz), 2.08–2.94 (2H, m), 3.16–3.64 (1H, m), 7.15 (1H, d, J=9Hz), 7.74 (1H, dd, J=9Hz and 2Hz), 7.98 (1H, d, J=2Hz), 10.91 (1H, s)

Analysis Calcd. for C$_{12}$H$_{11}$N$_3$O$_2$S: C, 55.16; H, 4.24; N, 16.08; S, 12.27, Found: C, 54.98; H, 4.24; N, 16.04; S, 12.52.

EXAMPLE 2

The following compounds were obtained according to a similar manner to that of Example 1.

(1)
3-Methyl-5-(4-methyl-6-oxo-1,4,5,6-tetrahydro-3-pyridazinyl)benzothiazolone mp 210° to 212° C.

IR (Nujol): 3180, 3060, 1690, 1680 cm$^{-1}$ (2)
3-Ethoxycarbonylmethyl-5-(4-methyl-6-oxo-1,4,5,6-tetrahydro-3-pyridazinyl)benzothiazolone mp 194° to 196° C.

IR (Nujol): 3175, 3050, 1750, 1670 cm$^{-1}$ (3)
3-(2-Methoxyethyl)-5-(4-methyl-6-oxo-1,4,5,6-tetrahydro-3-pyridazinyl)benzothiazolone mp 157° to 159° C.

IR (Nujol): 3180, 3060, 1690, 1665 cm$^{-1}$ (4)
3-[{4-(2-Hydroxyethyl)piperizin-1-yl}carbonylmethyl]-5-(4-methyl-6-oxo-1,4,5,6-tetrahydro-3-pyridazinyl)benzothiazolone mp 231° to 233° C.

IR (Nujol): 3220, 3080, 1670, 1650 cm$^{-1}$ (5)
3-Isopropyl-5-(4-methyl-6-oxo-1,4,5,6-tetrahydro-3-pyridazinyl)benzothiazolone mp 201° to 203° C.

IR (Nujol): 3220, 3080, 1690 cm$^{-1}$

EXAMPLE 5

Methyl iodide (0.14 ml) was added to a suspension of 5-(4-methyl-6-oxo-1,4,5,6-tetrahydro-3-pyridazinyl)benzothiazolone (0.60 g) and potassium carbonate (0.32 g) in N,N-dimethylformamide (25 ml) and the mixture was stirred at room temperature for 30 minutes.

After the solvent was evaporated in vacuo, water (50 ml) was added to the residue and the resultant mixture was extracted with ethyl acetate. The extract was washed with water, dried over magnesium sulfate and evaporated in vacuo to give slightly yellow powder (0.58 g), which was recrystallized from tetrahydrofuran to give 3-methyl-5-(4-methyl-6-oxo-1,4,5,6-tetrahydro-3-pyridazinyl)benzothiazolone (0.45 g) as colorless prisms.

mp 210° to 212° C.

IR (Nujol): 3180, 3060, 1690, 1680 cm$^{-1}$

NMR (DMSO-d$_6$, δ): 1.09 (3H, d), 2.07–2.92 (3H, m), 3.40 (3H, s), 7.25 (1H, d, J=9Hz and 2Hz), 8.00 (1H, d, J=2Hz), 10.87 (1H, s)

Analysis Calcd. for C$_{13}$H$_{13}$N$_3$O$_2$S: C, 56.71; H, 4.76; N, 15.26, Found: C, 57.07; H, 4.89; N, 15.67.

EXAMPLE 4

The following compound was obtained by reacting 5-(4-methyl-6-oxo-1,4,5,6-tetrahydro-3-pyridazinyl)benzothiazolone with ethyl bromoacetate according to a similar manner to that of Example 3.

3-Ethoxycarbonylmethyl-5-(4-methyl-6-oxo-1,4,5,6-tetrahydro-3-pyridazinyl)benzothiazolone mp 194° to 196° C.

IR (Nujol): 3175, 3050, 1750, 1670 cm$^{-1}$

NMR (DMSO-d$_6$, δ): 1.10 (3H, d, J=7Hz), 1.21 (3H, t, J=7Hz), 2.08–3.53 (3H, m), 4.20 (2H, q, J=7Hz), 4.88 (2H, s), 7.38 (1H, d, J=9Hz), 7.82 (1H, dd, J=9Hz and 2Hz), 8.10 (1H, d, J=2Hz), 10.93 (1H, s)

Analysis Calcd. for C$_{16}$H$_{17}$N$_3$O$_4$S.1/5 H$_2$O: C, 54.75; H, 5.00; N, 12.00; S, 9.14; H$_2$OI, 1.03, Found: C, 55.07; H, 4.77; N, 12.11; S, 9.66; H$_2$O, 0.98.

EXAMPLE 5

The following compound was obtained by reacting 5-(4-methyl-6-oxo-1,4,5,6-tetrahydro-3-pyridazinyl)benzothiazolone with 2-methoxyethyl bromide according to a similar manner to that of Example 3.

3-(2-Methoxyethyl)-5-(4-methyl-6-oxo-1,4,5,6-tetrahydro-3-pyridazinyl)benzothiazolone mp 157° to 159° C.

IR (Nujol): 3180, 3060, 1690, 1665 cm$^{-1}$

NMR (DMSO-d$_6$, δ): 1.12 (3H, d, J=8Hz), 2.10–3.58 (3H, m), 3.22 (3H, s), 3.63 (2H, t, J=5Hz), 4.15 (2H, t, J=5Hz), 7.38 (1H, d, J=9Hz), 7.77 (1H, dd, J=9Hz and 2Hz), 8.03 (1H, d, J=2Hz), 10.90 (1H, s)

Analysis Calcd. for C$_{15}$H$_{17}$N$_3$O$_3$S: C, 56.41; H, 5.36; N, 13.16, Found: C, 56.08; H, 5.34; N, 13.05.

EXAMPLE 6

The following compounds were obtained according to a similar manner to that of Example 3.

(1)

3-[{4-(2-Hydroxyethyl)piperazin-1-yl}carbonylmethyl]-5-(4-methyl-6-oxo-1,4,5,6-tetrahydro-3-pyridazinyl)benzothiazolone mp 231° to 233° C.

IR (Nujol): 3220, 3080, 1670, 1650 cm$^{-1}$ (2)

3-Isopropyl-5-(4-methyl-6-oxo-1,4,5,6-tetrahydro-3-pyridazinyl)benzothiazolone mp 201° to 203° C.

IR (Nujol): 3220, 3080, 1690 cm$^{-1}$

NMR (DMSO-d$_6$, δ): 1.12 (3H, d, J=7.5 Hz), 1.55 (6H, d, J=7.5 Hz), 2.08–3.55 (3H, m), 4.82 (1H, septet, J=7.5 Hz), 7.53 (1H, d, J=8 Hz), 7.82 (1H, dd, J=2 Hz, 8 Hz), 8.07 (1H, d, J=2 Hz) and 11.00 (1H, s)

Analysis Calcd. for C$_{15}$H$_{17}$N$_3$O$_2$S C, 59.38; H, 5.65; N, 13.85, Found: C, 59.71; H, 5.66; N, 13.65.

EXAMPLE 7

A mixture of 3-ethoxycarbonylmethyl-5-(4-methyl-6-oxo-1,4,5,6-tetrahydro-3-pyridazinyl)benzothiazolone (2.50 g) and 1-(2-hydroxyethyl)piperazine (2.81 g) was heated at 100° C. for 5 hours. The reaction mixture was chromatographed on silica gel by eluting with a mixture of chloroform and methanol (9:1) to give slightly yellow products (3.00 g), which were recrystallized form ethanol to give 3-[{4-(2-hydroxyethyl)piperazin-1-yl}carbonylmethyl]-5-(4-methyl-6-oxo-1,4,5,6-tetrahydro-3-pyridazinyl)benzothiazolone (2.10 g) as slightly yellow crystals.

mp 231° to 233° C.

IR (Nujol): 3220, 3080, 1670, 1650 cm$^{-1}$

NMR (DMSO-d$_6$, δ): 1.09 (3H, d, J=7 Hz), 2.10–3.60 (15H, m), 4.42 (1H, t, J=5 Hz), 4.92 (2H, s), 7.23 (1H, d, J=9 Hz), 7.77 (1H, dd, J=9 Hz and 2 Hz), 8.07 (1H, d, J=2 Hz), 10.93 (1H, s)

Analysis Calcd. for C$_{20}$H$_{25}$N$_5$O$_4$S.1/10 H$_2$O: C, 55.43; H, 5.86; H, 16.16; S, 7.40; H$_2$O, 0.42, Found: C, 55.59; H, 5.85; N, 16.07; S, 7.85; H$_2$O, 0.32.

What we claim is:

1. A compound of the formula:

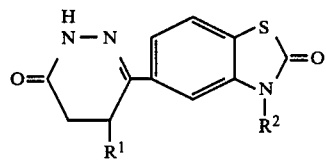

wherein
R$^1$ is lower alkyl, and
R$^2$ is hydrogen, lower alkyl, carboxy(lower)alkyl, lower alkoxy(lower)alkyl, aliphatic acyl(lower)alkyl, aromatic acyl(lower)alkyl or heterocyclic acyl(lower)alkyl,
and pharmaceutically acceptable salts thereof.

2. A compound of claim 1, wherein R$^2$ is hydrogen.

3. A compound of claim 2, which is 5-(4-methyl-6-oxo-1,4,5,6-tetrahydro-3-pyridazinyl)benzothiazolone.

4. A compound of claim 1, wherein R$^2$ is lower alkyl, lower alkoxy(lower)alkyl, lower alkoxycarbonyl(lower)alkyl or hydroxy(lower)alkylpiperazinylcarbonyl(lower)alkyl.

5. A compound of claim 4, which is selected from the group consisting of:
3-methyl-5-(4-methyl-6-oxo-1,4,5,6-tetrahydro-3-pyridazinyl)benzothiazolone,
3-isopropyl-5-(4-methyl-6-oxo-1,4,5,6-tetrahydro-3-pyridazinyl)benzothiazolone,
3-ethoxycarbonylmethyl-5-(4-methyl-6-oxo-1,4,5,6-tetrahydro-3-pyridazinyl)benzothiazolone,
3-(2-methoxyethyl)-5-(4-methyl-6-oxo-1,4,5,6-tetrahydro-3-pyridazinyl(benzothiazolone and
3-[{4-(2-hydroxyethyl)piperazin-1-yl}carbonylmethyl]-5-(4-methyl-6-oxo-1,4,5,6-tetrahydro-3-pyridazinyl)benzothiazolone.

6. A pharmaceutical composition comprising an effective amount of a compound of claim 1 or pharmaceutically acceptable salt thereof in association with a pharmaceutically acceptable, substantially non-toxic carrier or excipient.

7. A method for treatment of hypertension, heart disease and thrombosis in human beings and animals which comprises administering to the subject the pharmaceutical composition of claim 6.

8. A compound of the formula:

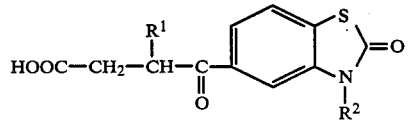

wherein
R$^1$ is lower alkyl, and
R$^2$ is hydrogen, lower alkyl, carboxy(lower)alkyl, lower alkoxy(lower)alkyl, aliphatic acyl(lower)alkyl, aromatic acyl(lower)alkyl or heterocyclic acyl(lower)alkyl,
and a salt thereof.

* * * * *